United States Patent [19]

Slavicek et al.

[11] Patent Number: 5,462,732
[45] Date of Patent: Oct. 31, 1995

[54] METHOD OF PROTECTING PLANTS FROM INSECTS BY APPLYING GYPSY MOTH VIRUS WITH ENHANCED POLYHEDRA PRODUCTION STABILITY

[75] Inventors: James M. Slavicek, Dublin; Melissa J. Mercer, Delaware, both of Ohio

[73] Assignee: The United States of America as represented by the Secretary of Agriculture, Washington, D.C.

[21] Appl. No.: 378,227

[22] Filed: Jan. 25, 1995

Related U.S. Application Data

[62] Division of Ser. No. 290,634, Aug. 15, 1994, Pat. No. 5,420,031, which is a continuation of Ser. No. 15,961, Feb. 8, 1993, abandoned.

[51] Int. Cl.⁶ .................................................. A01N 63/00
[52] U.S. Cl. ............................................................ 424/93.2
[58] Field of Search ............................................. 424/93.2

[56] References Cited

U.S. PATENT DOCUMENTS 5,132,220  7/1992  Shapiro et al. ..................... 435/235.1

OTHER PUBLICATIONS

Podgwaite et al., J. of Economic Entomology (Aug., 1992), vol. 85(4): pp. 1136–1139.

Cusack et al., J. of General Virology (Nov., 1989), vol. 70:pp. 2963–2972.

Lynn, J. of Invertebrate Pathology (May, 1994), vol. 63:pp. 268–274.

Primary Examiner—Richard A. Schwartz
Assistant Examiner—Terry McKelvey
Attorney, Agent, or Firm—Janet I. Stockhausen; M. Howard Silverstein; John D. Fado

[57] ABSTRACT

A virus having the identifying characteristics of ATCC VR2396 is disclosed. This virus has the trait of enhanced polyhedra production stability and resists forming a few polyhedra mutant virus. A method of protecting crops from insects comprising applying an insecticidally effective amount of virus having the identifying characteristics of ATCC VR2396 is also disclosed.

3 Claims, 8 Drawing Sheets

| NUMBER OF POLYHEDRA/CELL ± SD (1) | | | |
|---|---|---|---|
| DAYS POST INFECTION | A21-2 | A21-MPV | LEVEL OF SIGNIFICANT DIFFERENCE BETWEEN A21-2 & A21-MPV VALUES |
| 3 | 7.8 ± 5.8 | 24.1 ± 6.3 | $P < 0.01$ |
| 5 | 3.6 ± 2.2 | 27.4 ± 5.2 | $P < 0.02$ |
| 7 | 5.2 ± 3.1 | 46.4 ± 8.2 | $P < 0.02$ |

| PERCENTAGE OF CELLS WITH POLYHEDRA ± SD (1) | | | |
|---|---|---|---|
| DAYS POST INFECTION | A21-2 | A21-MPV | LEVEL OF SIGNIFICANT DIFFERENCE BETWEEN A21-2 & A21-MPV VALUES |
| 3 | 3.1 ± 1.6 | 31.5 ± 3.8 | P < 0.004 |
| 5 | 38.0 ± 3.3 | 72.2 ± 4.2 | P < 0.008 |
| 7 | 64.3 ± 3.8 | 85.7 ± 2.8 | P < 0.003 |

| BUDDED VIRUS TCID/50 PRODUCED/ML (1) | | | |
|---|---|---|---|
| DAYS POST INFECTION | A21-2 | A21-MPV | LEVEL OF SIGNIFICANT DIFFERENCE BETWEEN MEANS |
| 1 | $2.4 \times 10^5 \pm 8.6 \times 10^4$ | $3.9 \times 10^5 \pm 1.0 \times 10^5$ | NOT SIGNIFICANT |
| 3 | $1.7 \times 10^8 \pm 1.1 \times 10^8$ | $3.2 \times 10^7 \pm 6.5 \times 10^6$ | $P < 0.09$ |
| 5 | $2.4 \times 10^8 \pm 1.1 \times 10^7$ | $2.7 \times 10^7 \pm 1.0 \times 10^7$ | $P < 0.01$ |
| 7 | $2.2 \times 10^8 \pm 6.4 \times 10^7$ | $1.1 \times 10^7 \pm 4.6 \times 10^6$ | $P < 0.02$ |

| PASSAGE NUMBER | MEAN NUMBER OF POLYHEDRA/CELL ± SD (1,2) | | |
|---|---|---|---|
| | A21 | A21-MPV | LEVEL OF SIGNIFICANT DIFFERENCE BETWEEN A21 AND A21-MPV VALUES |
| 1 | 51.9 ± 13.4 (a) | 57.7 ± 8.5 (a) | NOT SIGNIFICANT |
| 2 | 18.3 ± 3.6 (b) | 38.1 ± 6.9 (a) | P < 0.04 |
| 3 | 11.7 ± 2.5 (bc) | 44.9 ± 20.6 (a) | P < 0.04 |
| 4 | 9.1 ± 3.0 (cd) | 35.2 ± 12.1 (a) | P < 0.02 |
| 5 | 6.4 ± 2.4 (d) | 35.4 ± 16.0 (a) | P < 0.04 |

| PERCENTAGE OF CELLS WITH POLYHEDRA ± SD (1,2) | | | |
|---|---|---|---|
| PASSAGE NUMBER | A21 | A21-MPV | LEVEL OF SIGNIFICANT DIFFERENCE BETWEEN A21 AND A21-MPV VALUES |
| 1 | 81.3 ± 4.0 (a) | 78.0 ± 4.0 (a) | NOT SIGNIFICANT |
| 2 | 63.0 ± 0.3 (b) | 88.3 ± 2.4 (b) | $P < 0.002$ |
| 3 | 59.3 ± 3.2 (b) | 88.8 ± 0.8 (b) | $P < 0.002$ |
| 4 | 56.8 ± 2.8 (b) | 86.5 ± 3.3 (b) | $P < 0.007$ |
| 5 | 51.2 ± 12.1 (b) | 84.0 ± 4.8 (b) | $P < 0.02$ |

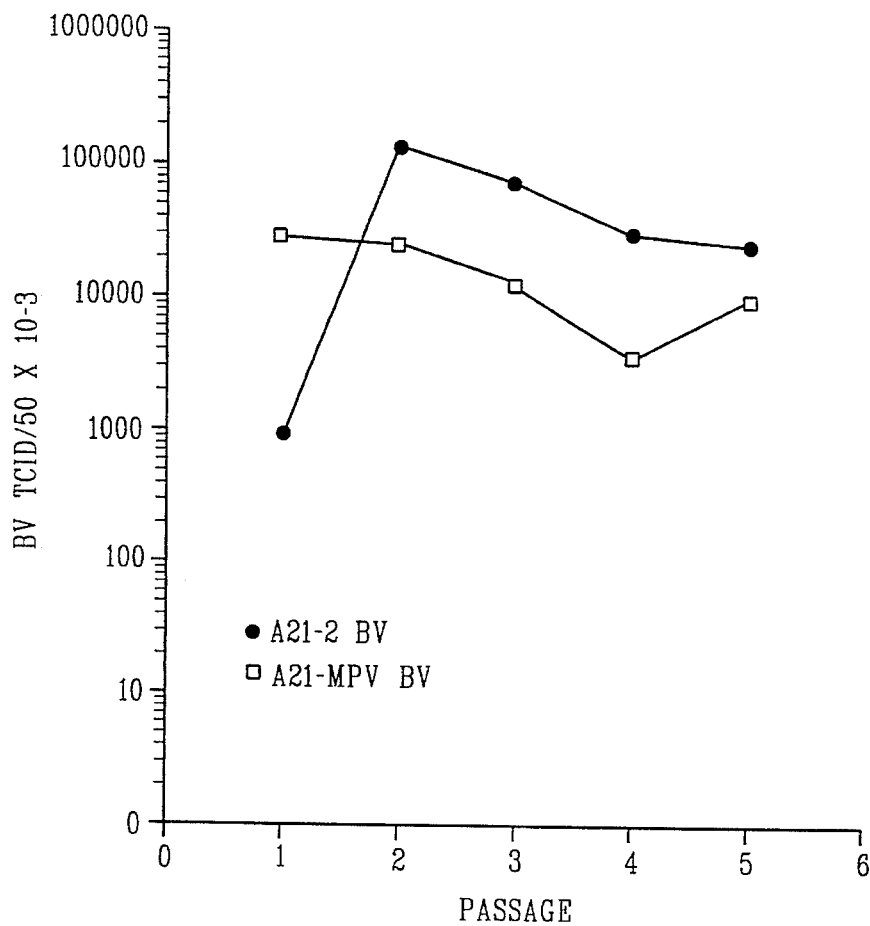

FIG. 7A

| BUDDED VIRUS TCID/50 PRODUCED/ML (1,2) ||||
|---|---|---|---|
| PASSAGE NUMBER | A21 | A21-MPV | LEVEL OF SIGNIFICANT DIFFERENCE BETWEEN MEANS |
| 1 | $8.5 \times 10^5 \pm 9.1 \times 10^5$ (a) | $2.9 \times 10^7 \pm 4.5 \times 10^7$ | NOT SIGNIFICANT |
| 2 | $1.4 \times 10^8 \pm 7.0 \times 10^7$ (b) | $2.6 \times 10^7 \pm 8.7 \times 10^7$ | $P < 0.05$ |
| 3 | $7.3 \times 10^7 \pm 6.7 \times 10^7$ (ab) | $1.2 \times 10^7 \pm 1.6 \times 10^7$ | $P < 0.09$ |
| 4 | $3.2 \times 10^7 \pm 3.2 \times 10^7$ (b) | $3.8 \times 10^6 \pm 2.3 \times 10^6$ | $P < 0.02$ |
| 5 | $2.9 \times 10^7 \pm 3.5 \times 10^6$ (b) | $1.1 \times 10^7 \pm 4.9 \times 10^6$ | $P < 0.02$ |

METHOD OF PROTECTING PLANTS FROM INSECTS BY APPLYING GYPSY MOTH VIRUS WITH ENHANCED POLYHEDRA PRODUCTION STABILITY

This application is a divisional of U.S. Ser. No. 08/290,634, filed Aug. 15, 1994, now U.S. Pat. No. 5,420,031, which is a continuation of U.S. Ser. No. 08/015,961, filed Feb. 8, 1993, now abandoned.

FIELD OF THE INVENTION

The general field of the present invention is methods of controlling plant pests, such as gypsy moths. Specifically, the field of the present invention is gypsy moth virus strains.

BACKGROUND

Chemical pesticides and fungicides are the most commonly used control agents for forest insect pests and fungal diseases. In excess of 350 billion pounds of these agents are used annually in the United States to control pests and diseases in forestry, agriculture, and residential areas. Broad spectrum insecticides and fungicides have adverse impacts not only on their target organisms but also on beneficial insects and fungi and, consequently, on the entire ecosystem. In addition, chemical residues may cause health problems among the human population.

Interest in biological insect and fungal control agents is growing as a consequence of concerns regarding chemical pesticide use. A number of bacteria synthesize antifungal compounds and over 1500 microorganism and microbial products have been identified that are insecticidal. Generally, natural control agents have little adverse ecological impact due to their specificity for the target host. Long term environmental hazards and health concerns are not a factor with biological control agents because chemical residues are not present. Unfortunately, biological control agents suffer from several disadvantages in comparison to chemical pesticides, including cost of production, efficacy, and stability.

One particularly troublesome plant pest is the gypsy moth *Lymantria dispar*. The gypsy moth was first imported from Europe into North America near Boston in 1869. Since then, the area of gypsy moth infestation has increased to include almost the entire New England area, New York, Delaware, Maryland, New Jersey, Pennsylvania, Virginia, West Virginia, Ohio, and Michigan. (McFadden, et al., *Forest Insect Guilds: Patterns of Interaction with Host Trees*, Y. N. Baranchikov, et al. pp. 172–186. US Department of Agriculture, For. Serv. Gen. Tech. Rep. NE-153, Radnor, Pa., 1989.) Several chemical insecticides have been used for gypsy moth control. DDT is one of the most effective chemical insecticides used against gypsy moths.

Knowledge of the environmental impacts of DDT and other chemical insecticides has caused all industry shift to the use of agents such as Dimilin and *Bacillus thuringiensis* (Bt) for gypsy moth control. The *Lymantria dispar* nuclear polyhedrosis virus (LdNPV), which is pathogenic to *Lymantria dispar* (gypsy moth), is also used as a biocontrol agent. LdNPV has the significant advantage over other control agents of specificity for the gypsy moth. Consequently, LdNPV is the agent of choice for all areas and particularly for use in environmentally sensitive areas. However, LdNPV is not used extensively for gypsy moth control because of high production costs and low efficacy. One particular problem with LdNPV propagation in cell culture is the propensity of the virus to mutate into a form that produces fewer polyhedra (FP mutants).

For gypsy moth virus production to be competitive, means of reducing production costs must be devised. One approach is the development of insect cell lines that produce high amounts of polyhedra. Lynn et al., (*Appl. Envron. Microbiol.*, 55, 1049–1051, 1989) have developed a fatbody cell line that produces greater amounts of polyhedra than other gypsy moth cell lines.

What is needed in the art of gypsy moth control is an improved strain of LdNPV capable of enhanced production.

SUMMARY OF THE INVENTION

The present invention is a virus having the identifying characteristics of ATCC VR2396. This virus has the trait of enhanced resistant to mutation to an FP form of LdNPV virus.

The present invention is also a virus derived from ATCC VR2396, wherein the virus retains the characteristics of polyhedra production stability.

The present invention is also a method of protecting plants from insects, comprising applying to an insect or an insect habitat an insecticidally effective amount of a virus having the identifying characteristics of ATCC VR2396. In a preferred form of the invention, the insects are gypsy moths.

The present invention is also an insecticidal composition comprising an insecticidal amount of a virus having the identifying characteristics of ATCC VR2396 and an inert carrier.

It is an object of the present invention to control insect pests.

It is another object of the present invention to provide an LdNPV virus with enhanced polyhedra production stability.

It is another object of the present invention to provide an LdNPV virus with enhanced resistance to mutating to an FP form of LdNPV virus.

It is an advantage of the present invention that insect control may be provided at lower cost.

It is another advantage of the present invention that ATCC VR2396 may be propagated with a fewer amount of FP mutants forming.

Other objects, advantages and features of the present invention will become apparent after review of the specification, drawings and claims.

BRIEF DESCRIPTION OF THE DRAWINGS

FIG. 7A is a graphical comparison of budded virus produced by isolates A21 and A21-MPV during serial passage in *L. dispar* 652Y cells; FIG. 7B is a tabular form of the same data.

FIG. 8 indicates the percentage of A21 plaques exhibiting the FP phenotype compared to the number of A21-MPV plaques exhibiting the FP phenotype during serial passages.

DESCRIPTION OF THE INVENTION

1. Brief Overview

Figures 1A, 1B:
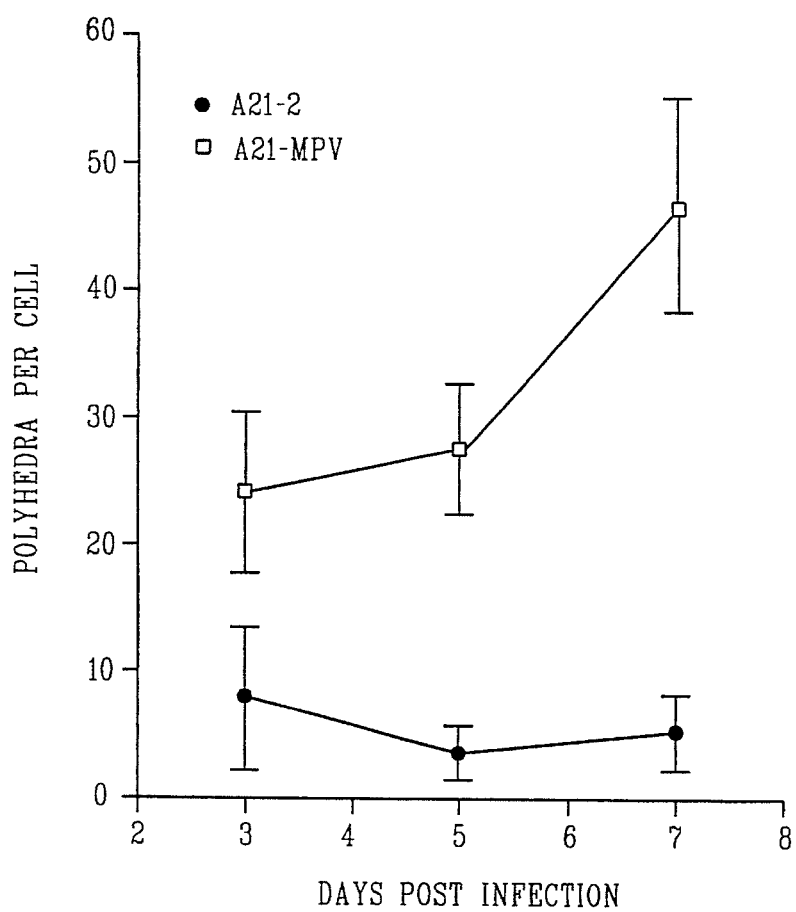
FIG. 1A is a graphical comparison of the amount of polyhedra produced in cells infected with A21-MPV after 14 serial passages versus cells infected with A21-2 after 6 serial passages in *L. dispar* 652Y cells.
FIG. 1B is a tabular form of the same data.

We have identified an LdNPV isolate, derived from LdNPV isolate A21, that exhibits an enhanced stability of wildtype polyhedra production levels during passage in *L. dispar* 652Y cells. All wild-type LdNPV isolates studied to date rapidly mutate during serial passage in 652Y cells to few polyhedra (FP) viral mutants. FP mutants exhibit the characteristics of production of an average of 4–10 polyhedra per cell, of polyhedra that are virtually devoid of viral nucleocapsids, and of a greater amount of budded virus compared to wild-type virus. In contrast, wild-type virus produce an average of 30–60 polyhedra per cell that contain many viral nucleocapsids and a lower amount of budded virus compared to FP mutants.

The unique attribute of our new isolate, A21-MPV, is a reduced tendency to mutate to an FP mutant during serial passage. Consequently, during production of LdNPV polyhedra, which requires serial passage, isolate A21-MPV will produce a far greater number of polyhedra than wildtype virus. In addition, a greater percentage of 652Y cells infected with isolate A21-MPV produce polyhedra in comparison to the percentage of cells that produce polyhedra after infection with wild-type LdNPV.

2. In General

Two forms of LdNPV (occluded and non-occluded virus) are produced during viral replication. (Granados, et al., *The Biology of Baculoviruses*, R. R. Granados and B. A. Federici (eds.) pp. 89–108. CRC Press, Boca Raton, Fla., 1986.) Early after viral infection, non-occluded virus is produced. This virus leaves the cell and is responsible for secondary infections within the hemocoel of the host insect. A different form of virus is produced late in infection that is occluded into a protein matrix composed primarily of a viral-encoded protein. These structures, approximately 1 to 3 micrometers in diameter and polyhedral in shape, are termed "polyhedral occlusion bodies" or "polyhedra". Nucleocapsids within polyhedra are protected from most environmental conditions with the exception of ultraviolet light.

Gypsy moth virus is applied through sprayers in the field in the form of polyhedra, which are ingested by gypsy moth larvae feeding on tree foliage. Once within the alkaline environment of the insect midgut, the polyhedra dissolve and release nucleocapsids which infect the insect midgut cells, thereby initiating the infection process.

For commercial applications, LdNPV is currently produced in gypsy moth larvae at a cost of approximately $30.00 for enough polyhedra to treat an acre of forest. Production is the most expensive component in the commercial use of LdNPV. Virus production is limited by the efficiency of production of polyhedra in larvae. Efforts to produce polyhedra in cell culture systems are being made to generate a more economical production methodology. In comparison, production costs of Dimilin and Bt are approximately $3.00 per acre equivalent.

However, problems exist in obtaining virus from cell culture. A class of mutant baculoviruses called few polyhedra (FP) mutants are generated at high frequency during viral replication in insect cell culture. FP mutants have the characteristics of producing few polyhedra that contain few or no viral nucleocapsids and are noninfectious. In addition, FP mutants produce a greater amount of budded virus (non-occluded virus) compared to wild type virus.

FP mutants have been generated during serial passage of the *Autographa californica* nuclear polyhdrosis virus (AcMNPV), *Trichoplusia pi* MNPV (TnMNPV), *Galleria mellonella* MNPV (GmMNPV), and *Lymantria dispar* MNPV. Studies on AcMNPV have shown that FP mutants are often generated through the insertion of host DNA sequences into the viral genome. The frequency of FP mutant genesis during viral serial passage is specific to the virus species being passed. Table 1 below summarizes the frequency of FP mutant formation as a function of serial passage.

TABLE 1

| Virus | Passages Necessary to Accumulate FP Mutant Percentages of: | | | |
|---|---|---|---|---|
| | 25% | 50% | 75% | >90% |
| GmNMPV[a] | 4.5 | 5.5 | 7.0 | 8.0 |
| TnMNPV[b] | 4.0 | 5.0 | 6.0 | 10.0 |
| AcMNPV[c] | 1.0 | 1.5 | 3.5 | >4.0 |
| LdMNPV[d] | | 1.0 | | 2.0 |

[a]. Fraser, et al., (1982) Virology, 117, 366–378.
[b]. Potter, et al., (1976) J. Virology, 18, 1040–1050.
[c]. Hink, et al., (1976) J. Invertebrate Pathology, 27, 49–55.
[d]. Slavicek, J. M. Unpublished data.

Our approach to increase polyhedra production in cell culture is the development of a viral strain that exhibits a low frequency of FP mutant generation and consistently produces polyhedra without reductions as a consequence of passage. These traits are what we mean by "polyhedra production stability".

Our preliminary studies with LdNPV polyhedra production in 652Y cells found a reduction in the number of polyhedra produced as a function of virus passage number. When non-occluded virus is obtained from fourth-instar gypsy moth larvae (that were infected per os with polyhedra) and used to infect 652Y cells, the infected cells produce approximately 50 polyhedra per cell (Table 2). After five passages in cell culture, the number of polyhedra produced per cell decreased to approximately 6. The cost of cell culture production could be reduced if the initial high level of polyhedra formation could be stabilized.

We have identified a viral variant (termed A21-MPV, which stands for Many Polyhedra Variant) that maintains a high level of polyhedra synthesis after repeated passage in cell culture (Table 2). 652Y cells infected with MPV contain approximately 45 polyhedra per cell. In addition, more of the infected cells produce polyhedra in comparison to wild type isolate A21. Virus A21-MPV has been deposited with the American Type Culture Collection, Rockville, Md., on Dec. 16, 1992 at Accession Number VR2396 under the conditions of the Budapest Treaty. Deposit of this sample does not imply or grant a license to use the virus.

TABLE 2

| Isolate | 1st passage polyhedra production | Polyhedra production per cell after more than 5 passages | Percentage of cells containing polyhedra |
|---------|----------------------------------|----------------------------------------------------------|------------------------------------------|
| A21     | 52                               | 6                                                        | 51                                       |
| A21-MPV | 58                               | 45                                                       | 85                                       |

3. A21-MPV Isolation

LdNPV isolates A21, B21, 122, and 163 were purified to genotypic homogeneity by low dose infection of *L. dispar* larvae. Fourth instar larvae were fed diet containing a dose of LdNPV that caused approximately 4 to 10% mortality. Polyhedra were collected from individual cadavers, and used for a second round of low dose infections. Polyhedra were collected from individual cadavers, viral genomic DNA was isolated and analyzed to assess the degree of genotypic heterogeneity present. Isolates A21, B21,163 and 122 appeared to be genotypically homogenous and were used for further investigations.

The initial purpose of the experiment during which we isolated A21-MPV was to develop the methodology for generation of recombinant viruses. LdMNPV isolate A21 and a transplacement plasmid pLd-B-Gal that contains the beta galactosidase gene from *E. coli* were examined in this study.

*Lymantria dispar* 652Y cells were propagated in a modified insect cell culture medium, such as "GOODWIN'S IPL-52B" (JRH Biosciences) medium with 10% heat-inactivated fetal bovine serum and 6.25 mM glutamine. $2 \times 10^5$ cells were plated per well in P6 plates (Corning) prior to transfection. Media was removed and replaced with 1.5 ml serum free media, and 100 ul of lipofection solution (50 ul 10 mM Tris, 1 mM EDTA, pH 7.5; 2 ug, 5 ug, and 10 ug of LdMNPV DNA, and 4 ug, 2 ug, and 4 ug of pLd-B-Gal DNA for trials A, B, and C, respectively; and 50 ul of a transfection reagent, such as "LIPOFECTIN" reagent, Gibco BRL) was added to the P6 wells. After a 4 hour incubation period the media was replaced with complete media containing 50 ug/ml gentamicin. Fifteen days after transfection the cells were harvested and used for enzymatic B-galactosidase assays to detect the presence of recombinant LdMNPV containing the B-galactosidase gene. The percentage of recombinant virus present was calculated after determination of recombinant virus titer by plaque assay (using agarose containing a substrate for the enzyme β-galaxctosidase, such as "BLUO GAL" supplied by Gibco) and the total virus titer by TCID-50 Assay.

LdMNPV isolate A21-MPV was identified in this study. However, A21-MPV does not contain the beta-galactosidase gene. Isolate A21-MPV is a mutant derivative of isolate A21 that was detected during the course of the study described above. The genesis of A21-MPV is not related to the experimental manipulations used to generate a recombinant virus. Cells containing isolate A21-MPV were recognized through examination of infected cells by light microscopy. These cells were black in color, in contrast to all other cells infected with isolate A21, due to the large number of polyhedra present. The majority of infected cells, greater than 99.99%, contained from 4 to 10 polyhedra, which is characteristic of FP viral mutants. The virus that infected the cells containing a large number of polyhedra was purified and termed LdNPV isolate A21-MPV (many polyhedra variant, MPV). Isolate A21-MPV was serially passed in cell culture for 20 passages. The number of 652Y cells used for each passage were $1 \times 10^4$, $1 \times 10^5$, $1 \times 10^6$, and $5 \times 10^6$ for passages 1–8, 9–10, 11 and 12–20, respectively.

To generate cell culture lines of LdNPV isolates A21, B21, 163, and 122, budded virus was obtained from *L. dispar* larvae infected with these isolates and used to infect 652Y cells in culture. Budded virus from these initial infections was used to generate the plaque purified viral lines A21-2, B21-1, 122-2, and 163-2. After plaque purification the isolates were serially passed in cell culture for 6 passages. The number of 652Y cells infected at each passage were $1 \times 10^4$, $1 \times 10^5$, $1 \times 10^6$, and $5 \times 10^6$ for passages 1, 2, 3 and 4–6, respectively.

4. Restriction endonuclease analysis of isolate A21-MPV.

A21 and A21-MPV genomes were subject to restriction endonuclease digestion with BglII, EcoRI, EcoRV, HindIII, BamHI, and PstI, and the digestion profiles were compared to determine whether DNA restriction fragment length polymorphisms existed between the viruses. No differences in DNA fragment lengths were detected. This finding supports the hypothesis that isolate A21-MPV is a mutant derivative of isolate A21. The approach used in this comparison will detect DNA insertions or deletions of approximately 0.5 kb or greater in length, and nucleotide additions, deletions or alterations of the restriction endonuclease recognition sites of the enzymes used.

5. Bioassay data on isolate A21-MPV, A21, and Gypchek (a standard gypsy moth virus).

Comparative bioassays were performed as described in Slavicek et al., (1992, *J. Invertebrate Pathology* 59: 142–148). Briefly, polyhedra pastes of the various isolates were suspended in 10 ml of Sterile 0.05M Tris-HCl buffer, pH 7.2, and briefly sonicated to disperse the polyhedra. A 100-mg lyophilized sample of standard gypsy moth virus, such as Gypchek, was similarly suspended and vigorously ground in a glass tissue homogenizer for 3 min. Five serial 10-fold dilutions of each of the stock virus suspensions were prepared in Tris buffer. Dilutions were prepared such that final polyhedra concentrations in diet fed to test insects ranged between $1 \times 10^2$ and $1 \times 10^7$/ml. One milliliter of dilution was added to 99 ml of tempered (52° C.) diet and vigorously mixed with a variable-speed stirrer (5000 rpm) for 30 sec. Virus-treated diet was cooled and cooled and cut into 1.25-cm$^3$ cubes.

Each virus dosage was presented to five groups of 10 newly molted second instar larvae from a standard laboratory strain of the gypsy moth (New Jersey, $F_{34}$). Each group of 10 larvae was confined to a 100×15-mm plastic petri dish and given two 1.25-cm$^3$ virus-treated diet cubes on which to feed for 48 hr. Larvae were given untreated diet ad libitum for the remaining 12 days of the bioassay. Five groups of 10 larvae (controls) were fed untreated diet for 14 days. Larvae were reared in a growth chamber at 24±2° under a 16/8-hr light/dark photoperiod and observed daily for mortality. Dead larvae were removed and examined microscopically to confirm MPV deaths.

Mortality data were examined by Probit analysis using a statistical software program, such as "POLO-PC" (LeOra Software, Berkeley, Calif.). Potencies of isolates A21-MPV and A21 relative to standard Gypchek were estimated by comparing $LC_{50}$ values.

Gypchek is the name of the LdMNPV registered by the Forest Service and is used currently for gypsy moth control. Gypchek is available from U.S. Forest Service, Northeastern Forest Experiment Station, Hamden, Conn.

The results of the bioassay are tabulated in Table 3.

TABLE 3

| Isolate | LC-50[a] | Limits[b] | LC-90[a] | Limits |
|---|---|---|---|---|
| Gypchek | 3800 | 2500–6000 | 24,000 | 14,000–56,000 |
| A21 | 4700 | 2800–7800 | 32,000 | 17,000–82,000 |
| A21-MPV | 5000 | 3400–7600 | 39,000 | 23,000–86,000 |

[a]. LC-50 and LC-90 (lethal concentration) values are the number of polyhedra per ml of diet that cause 50% and 90% larval mortality, respectively.
[b]. Limit values are numbers of polyhedra per ml of diet that cause 50% and 90% larvae mortality, respectively.

The minor differences found in LC-50 and LC-90 values exhibited by isolates A21, A21-MPV and Gypchek were not significant. This finding indicates that the biological activity of A21-MPV is essentially the same as Gypchek, and consequently A21-MPV could be used for control of the gypsy moth.

6. Microscopy Comparison

Comparison of *L. dispar* 652Y cells infected with LdMNPV isolates A21-2 and A21-MPV via light microscopy demonstrates the difference in polyhedra production and, thus, the biological difference between the two viruses. 652Y cells were infected with 0.2 TCID-50 units per cell of A21-2 and A21-MPV. Seven days after infection the cells were examined by light microscopy and photographed at 100X magnification. The cells infected with isolate A21-2 contain very few polyhedra. In contrast, cells infected with A21-MPV contain a large number of polyhedra and appear black at this magnification level.

Electron micrographs of polyhedra cross-sections produced by isolate A21 and A21-MPV infection at passage 1 and passage 5 can also differentiate between the two strains. 652Y cells were infected with 0.2 TCID-50 units per cell of either A21 or A21-MPV. Seven days after infection polyhedra were harvested and prepared for examination by electron microscopy.

To prepare for electron microscopy, polyhedra were fixed in sodium cacodylate buffer, pH 7.2 (0.05M sodium cacodylate, 0.5 mM HCl), containing 1% glutaraldehyde at 4° C. for 20 min. Polyhedra were then fixed in sodium cacodylate buffer with 3% glutaraldehyde for 1 hr at 4° C. The samples were washed 3X in sodium cacodylate buffer over a 1-hr period. The samples were postfixed in sodium cacodylate buffer containing 2% osmium tetroxide for 2.5 hr at ambient temperature and then washed 3X in sodium cacodylate buffer over a 1-hr period. Molten agar was added to the samples (final concentration 2%) and allowed to gel. The samples then were cut into 1-mm² blocks and incubated overnight in 35% ethanol. The samples were dehydrated through incubation in an ethanol series (35, 50, and 70% with 2% uranylacetate, 85, 95, 100%-3X) for 5–7 min at each step, except for the 70% step which was for 1 hr. The samples were then washed 3X (10 min each wash) in propylene oxide.

The samples were infiltrated over a 24-hr period with propylene oxide: "Poly/Bed 812" (25.55 g "Poly Bed", 13.5 g dodecenylsuccinic anhydride, 10.9 g nadic methylanhydride, Polysciences) at 2:1, 1:1, and 1:2 ratios. After infiltration, the polyethylene capsules were flushed with freon and filled with plastic embedding medium, such as "POLY/ BED 812 containing 2% DMP 30 (Polysciences), incubated at 35° C. for approximately 15 hr, 45° C. for 8 hr and finally at 60° C. overnight. The samples were sectioned with a microtonme, such as a diamond knife on a Reichert-Jung "ULTRACUT E43", the sections stained for 20 min in 5% uranylacetate in methanol, poststained in lead nitrate (2.7% lead citrate, 3.5% sodium citrate, 0.16N NaOH), and viewed with a Hitachi model HU 11E-1 transmission electron microscope. Polyhedra cross sections were photographed, and the number of virions present within cross-sections were quantified by counting.

In the A21 samples, numerous viral nucleocapsids are evident in cross-sections produced at the first passage. In contrast, cross-sections of polyhedra produced at the fifth passage contain few or no viral nucleocapsids. In the A21-MPV sample, numerous viral nucleocapsids are evident in cross-sections produced at both the first passage and fifth passage. The presence of numerous viral nucleocapsids in polyhedra produced at the fifth passage by A21-MPV indicates that this isolate is producing normal polyhedra at this passage, in contrast to isolate A21.

7. Comparison of Polyhedra Production Attributes of Isolates A21-MPV and A21-2 After Plaque Purification in Cell Culture The number of polyhedra produced per cell within cells containing polyhedra, the percentage of cells with polyhedra, and the amount of budded virus produced by isolates A21-MPV after 14 passages in cell culture and isolate A21-2 after 6 passages in cell culture were determined and compared. The number of polyhedra per cell produced by isolates A21-MPV and A21-2 was determined 3, 5, and 7 days post infection (p.i.). On all days p.i. examined, cells infected with isolate A21-MPV contained significantly more polyhedra per cell within cells containing polyhedra compared to cells infected with isolate A21-2 (FIG. 1). At seven days p.i. cells infected with A21-MPV contained an average of 46.4 polyhedra, in contrast to 5.2 polyhedra per cell in cells infected with A21-2.

Figures 2A, 2B:
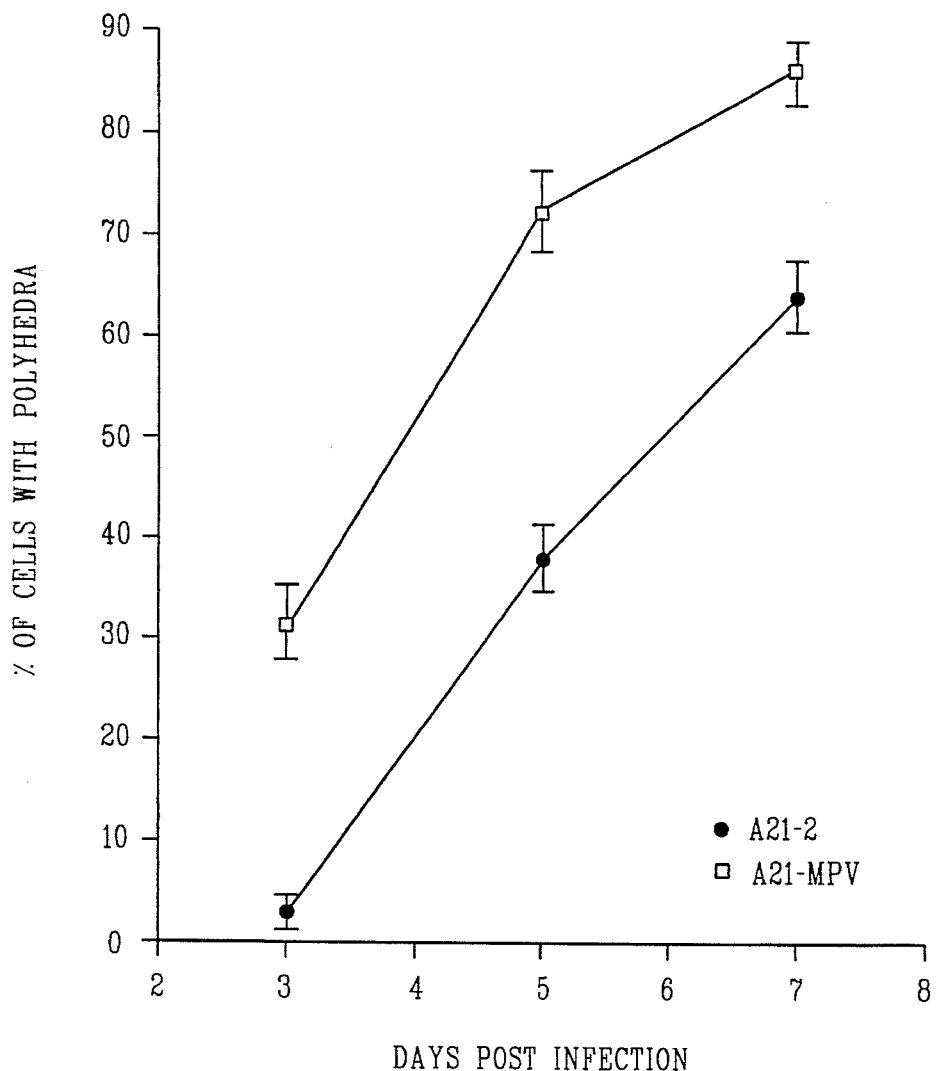
FIG. 2A is a graphical comparison of the number of cells found to contain polyhedra after infection with A21-MPV after 14 serial passages versus the number of cells found to contain polyhedra after infection with A21-2 after 6 serial passages in *L. dispar* 652Y cells.
FIG. 2B is a tabular form of the same data.

The percentage of cells containing polyhedra was determined 3, 5, and 7 days p.i. A significantly greater percentage of cells were found to contain polyhedra at 3, 5, infected with A21-2 (FIG. 2). At 7 days p.i. an average of 85.7% of cells infected with A21-MPV contained polyhedra. In contrast, 64.3% of cells infected with A21-2 contained polyhedra 7 days p.i.

Figures 3A, 3B:
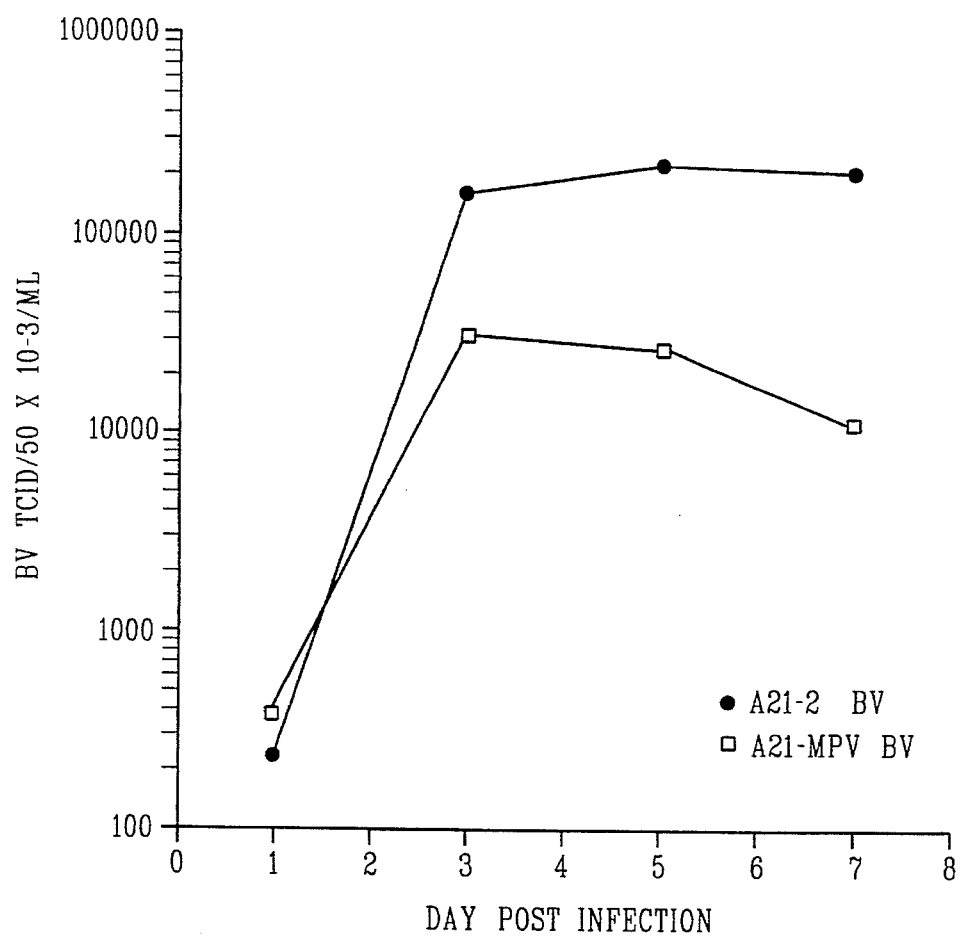
FIG. 3A is a graphical comparison of the amount of budded virus produced by isolates A21-MPV after 14 serial passages and A21-2 after 6 serial passages in *L. dispar* cells.
FIG. 3B is a tabular form of the same data.

The amount of budded virus produced by isolates A21-MPV and A21-2 was determined 1, 3, 5, and 7 days p.i. On days 3, 5, and 7 p.i., A21-2 produced a greater amount of budded virus in comparison to A21-MPV (FIG. 3). On days 5 and 7 p.i. A21-2 produced significantly more budded virus than A21-MPV.

Figure 4A:
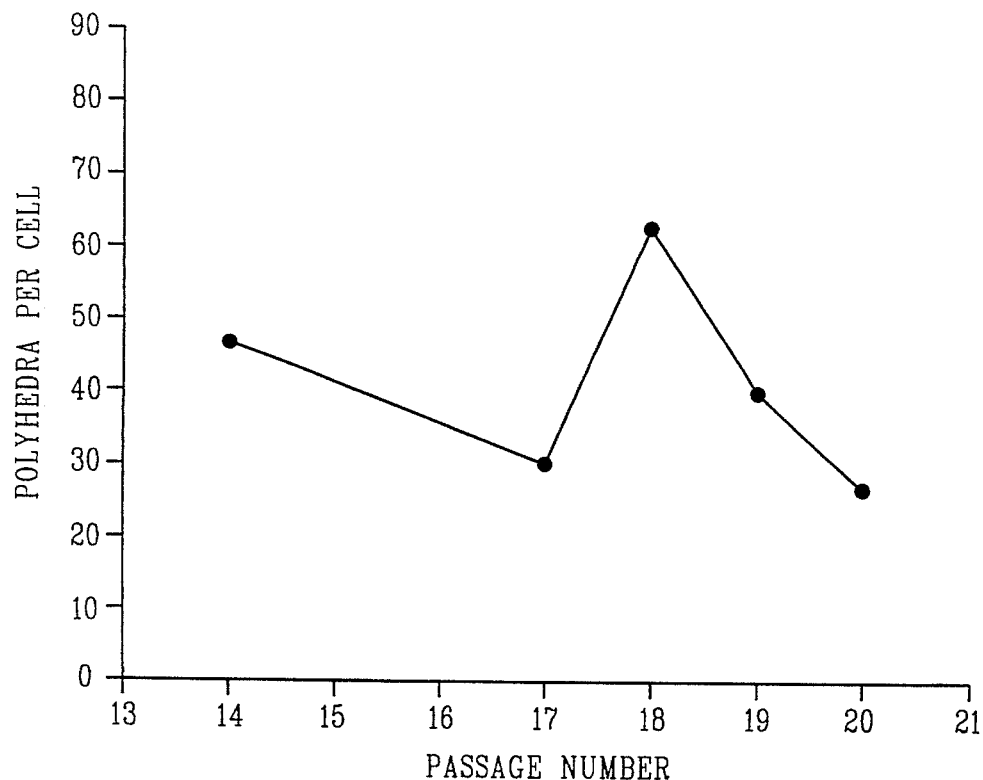
FIG. 4A demonstrates the retention of wild-type phenotype by A21-MPV through multiple passages.
Figure 4B:
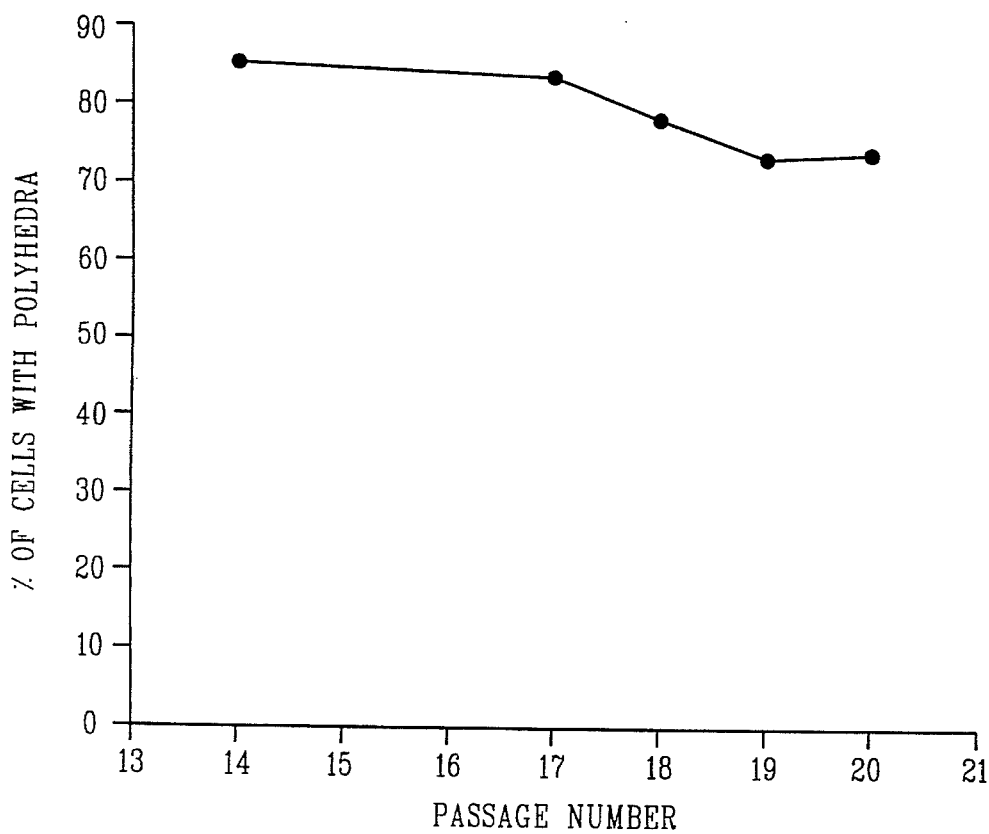
FIG. 4B demonstrates the percentage of cells with polyhedra after infection with A21-MPV during extended serial passage in *L. dispar* 652Y cells.

These results demonstrate that isolate A21-2 exhibits the attributes of an FP mutant at the 6th passage in cell culture. In contrast, A21-MPV has retained a wild-type polyhedra production phenotype through the 14th serial passage. A21-MPV was then serially passed an additional 6 times through passage 20. As shown in FIG. 4, A21-MPV retained a wild-type phenotype through the 20th passage. These results demonstrate the enhanced stability of polyhedra production exhibited by A21-MPV.

Isolates B21-1, 122-2 and 163-2 were serially passed in 652Y cells for 6 passages as described for isolate A21-2. Similarly to A21-2 isolates B21-1, 122-2, and 163-2 exhibited the attributes of FP mutants at the 6th passage. This result demonstrates the high frequency of FP mutants at the 6th passage and demonstrates the high frequency of FP mutant formation with wild-type strains of LdNPV in contrast to isolate A21-MPV.

8. Polyhedra Production Characteristics During Serial Passage

To further determine the stability of polyhedra production by A21-MPV and determine the number of passages necessary for a wild-type virus to mutate to an FP mutant, polyhedra production by isolates A21 and A21-MPV were examined through five passages in cell culture. Viral nucleocapsid occlusion characteristics of A21 and A21-MPV during serial passage are related below in Table 4. LdMNPV isolates A21 and A21-MPV were serially passed five times in L. dispar 652Y. L. dispar larvae were infected per os with A21 (non-plaque purified) polyhedra produced in larvae and A21-MPV polyhedra produced in cell culture. Five days after infection larvae were bled, and the hemolymph was used to infect $1\times10^6$ L. dispar 652Y cells at 0.2 TCID/50 units per cell. This first infection in cell culture was passage number 1. Budded virus from this infection was then used to infect new cells to generate passage 2. The remaining passages examined in this study, passages 3–5, were generated using budded virus from the previous passage as inoculum.

Polyhedra produced by these isolates after each passage were prepared for examination by electron microscopy as described above. The number of viral nucleocapsids present in polyhedra cross sections were determined, and are presented below in terms of the number of nucleocapsids present per square micrometer of cross section surface area (Table 4).

TABLE 4

Number of viral nucleocapsids per $um^2$ of cross section area

| Isolate | Passage 1 | Passage 2 | Passage 3 | Passage 4 | Passage 5 |
|---|---|---|---|---|---|
| A21 | 5.7 | 4.0 | 2.5 | 1.1 | 0.5 |
| A21-MPV | 5.2 | 2.9 | 5.7 | 6.1 | 3.1 |

The number of viral nucleocapsids present in polyhedra produced by A21 decreased during serial passage from an average of 5.7 at passage 1 to 0.5 at passage 5. In contrast, the number of nucleocapsids present in polyhedra produced by isolate A21-MPV remained essentially constant during five serial passages.

Figures 5A, 5B:
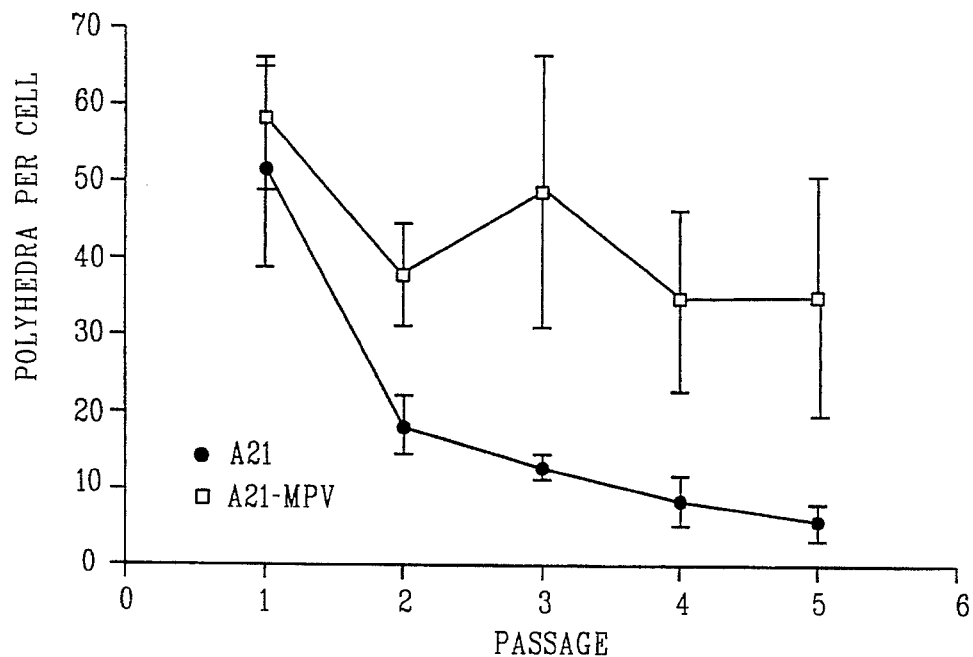
FIG. 5A is a graphical comparison of polyhedra per cell of cells infected with A21-MPV and cells infected with A21 during serial passage.
FIG. 5B is a tabular form of the same data.

L. dispar 652Y cells exhibited essentially the same number of polyhedra per cell at the first passage infection with isolates A21-MPV and A21 (FIG. 5). In contrast, at passages two through five, cells infected with A21-MPV contained significantly more polyhedra per cell compared to cells infected with A21 (FIG. 5). After five serial passages, cells infected with A21-MPV contained an average of 35.4 polyhedra. In contrast, cells infected with A21 contained an average of only 6.4 polyhedra per cell. After each serial passage, cells infected with A21 contained significantly fewer polyhedra in comparison to the previous passage. In contrast, no significant difference was found in the number of polyhedra per cell after infection with A21-MPV during five serial passages.

Figures 6A, 6B:
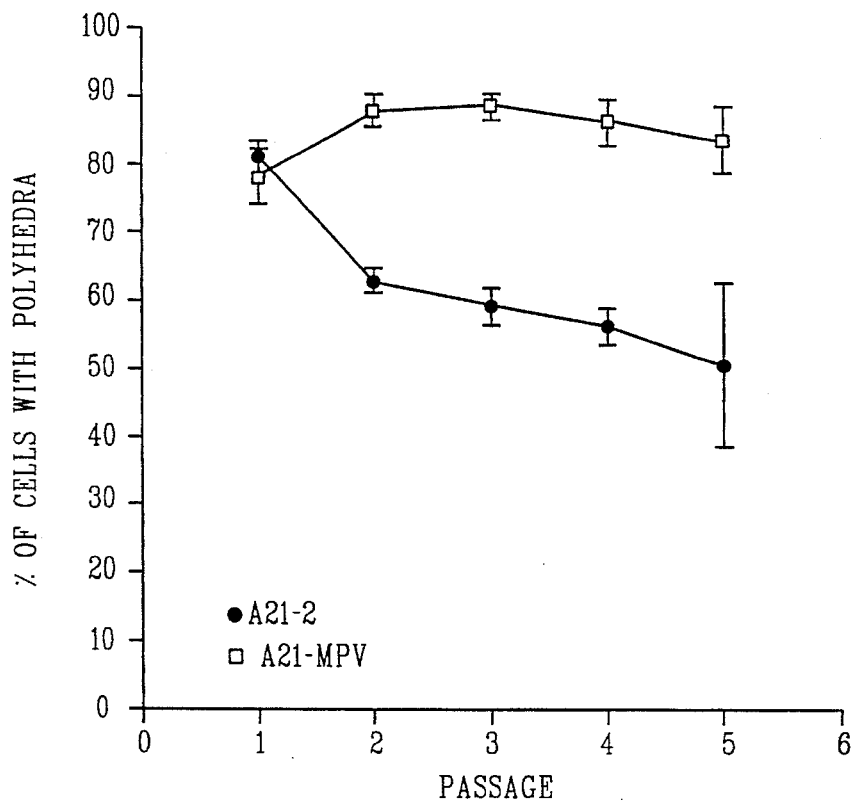
FIG. 6A is a graphical comparison of the percentage of polyhedra in cells infected with A21-MPV versus A21 during serial passage.
FIG. 6B is a tabular form of the same data.

At the first passage, cells infected with A21-MPV and A21 exhibited the same percentage of cells containing polyhedra. At passages two through five a significantly greater percentage of cells infected with A21-MPV contained polyhedra in comparison to cells infected with A21. At passage five, 84.0% of cells infected with A21-MPV contained polyhedra whereas only 51.2% of cells infected with A21 contained polyhedra. In addition, A21-MPV exhibited a significant increase in the percentage of cells containing polyhedra after the first passage. In contrast, A21 exhibited a significant reduction in the percentage of cells containing polyhedra after the first passage. FIG. 6 graphically displays these results.

Isolate A21-MPV exhibited stable budded virus production during five serial passages. The amount of budded virus produced by A21-MPV was less than the amount of budded virus produced by A21 at passages 2–5. This difference was found to be significant at passages 2, 4, and 5, and nearly significant at passage 3. In addition, A21 exhibited an increase in budded virus production after the first passage. FIG. 7 graphically displays these results.

Figure 8:
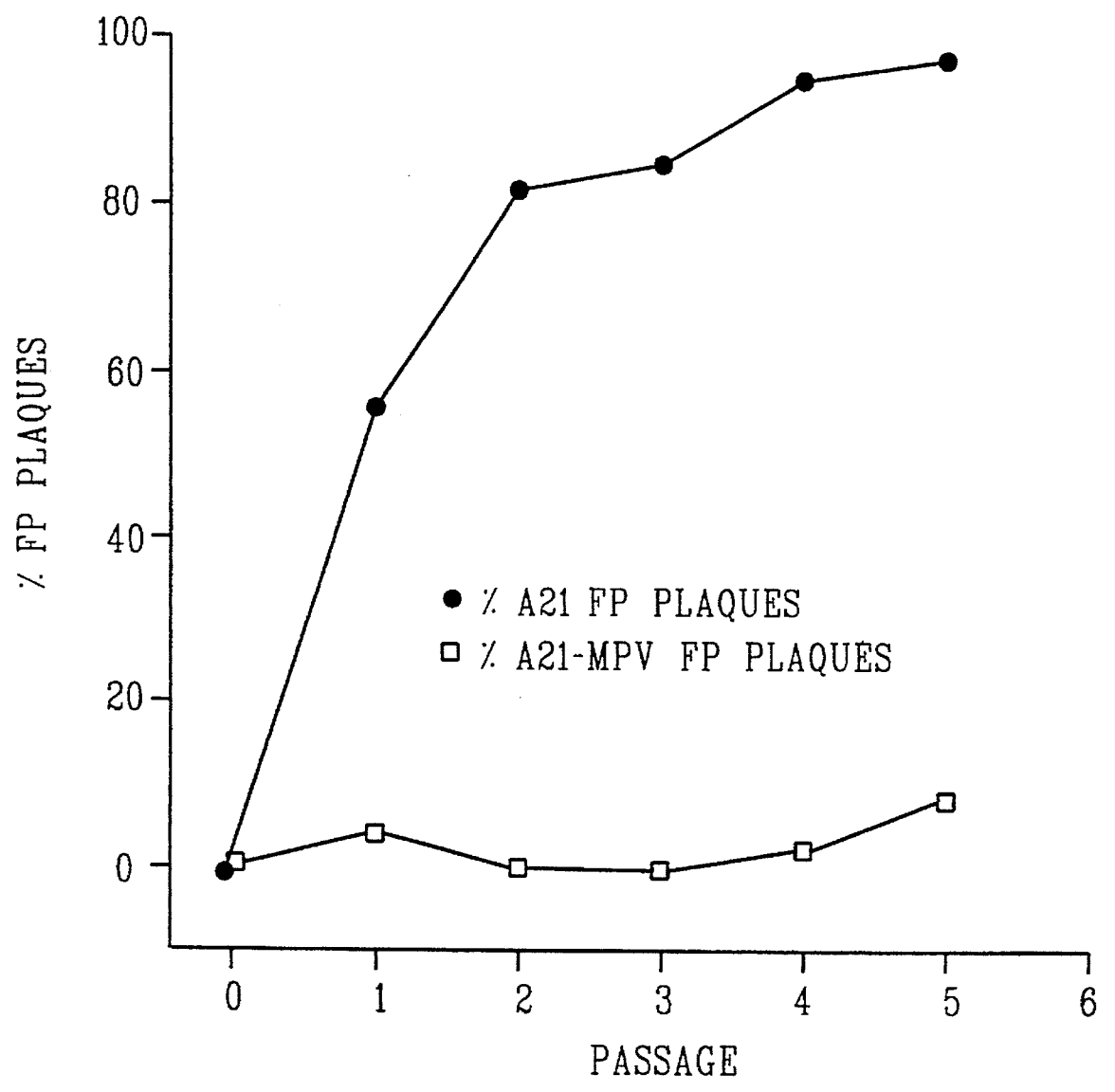

The percentage of A21-MPV and A21 viruses exhibiting the FP or MP phenotype was determined during serial passage. Budded virus produced at each serial passage was used to generate viral plaques. Ninety-six plaques of each isolate after each passage were used to infect L. dispar 652Y cells, and the infections were scored as exhibiting either the MP or FP phenotype. Budded virus obtained from insect hemolymph was used for passage zero for both viral isolates. As shown in FIG. 8, the percentage of A21 plaques exhibiting the FP phenotype rapidly increased during serial passage from zero to 82% after just two serial passages. In contrast, A21-MPV maintained the MP phenotype during cell passage.

9. Viral formulation and application for gypsy moth control

We envision that the A21-MPV isolate may be applied to insects or insect habitats in a manner similar as that currently used for LdMNPV. The virus must be ingested by the insect to be effective. However, insects may also become infected as a consequence of ingestion of virus present on the insect or on insect egg masses. Therefore, in the case of plants, the virus will typically be applied to leaf surfaces.

LdMNPV has been formulated as described below for gypsy moth control:

10 g Gypchek ($5.0\times10^{10}$ polyhedra per gram)

227 g (6% wt/vol) a UV light screen, such as "ORZAN LS" ITT Raynonier, Seattle, Wash.)

0.47 liters (12.5% by vol) a liquid supplement consisting of feed stock molasses, such as "PRO MO", (Southern States Cooperative, Richmond, Va.)

77.6 ml (2% by vol) a sticker-spreader, such as "RHOP-LEX B60A" Rohm & Haas Company, Philadelphia, Pa.) 3.24 liters (85.5% by vol) water A similar preparation is envisioned for the A21-MPV isolate.

The amount of virus to be administered to the insect or the insect habitat is an amount effective to reduce insect infestation as predetermined by routine testing. If the ultimate response is insect mortality, an "insecticidally effective amount" is defined to be those qualities of virus which will result in a significant mortality rate of a test group, as compared to an untreated group. The insecticidally effective amount may vary with the species of pest, stage of larval development, nature of the substrate, the type of vehicle or carrier, the period of treatment and other factors.

It is often advantageous to apply viral inoculants with a carrier. Suitable agronomically acceptable carriers are known in the art. Inert solids, such as cellulose or sugars, wetable powders, and aqueous surfactant mixtures are illustrative of suitable chemical carriers. Depending on many factors, the concentration of virus in the final composition may vary, but would include an insecticidally effective amount which may typically be between $1\times10^8$ to $1\times10^{11}$ polyhedra per liter, but the preferred embodiment would be between $1\times10^{10}$ to $1\times10^{11}$ polyhedra per liter.

Aerial application of Gypchek has been as follows: An airplane, such as 448 kW (600 hp) Grumman "AGCAT" airplane equipped with 8 atomizers, such as "AU 5000" atomizers manufactured by Micronair can be used for LdN-MPV application. Delivery of formulated virus could be from $1.0\times10^{11}$ to $5.0\times10^{11}$ polyhedra in 7.5 liters per acre at an airspeed of 160 km/h. (Podgwaite, et al., *J. Economic Entomology*, 85: 1136–1139).

We claim:

1. A method for protecting plants from insects against which LdMNPV is toxic, said method comprising applying to such insects or insect habitat an insecticidally effective amount of a virus designated ATCC VR2396 deposited at the American Type Culture Collection.

2. A method according to claim 1, wherein said insects are gypsy moths.

3. A method according to claim 2 wherein said insecticidally effective amount is an amount sufficient to achieve the desired level of plant protection.

* * * * *